(12) United States Patent
Minor et al.

(10) Patent No.: US 7,892,826 B2
(45) Date of Patent: Feb. 22, 2011

(54) HUMAN CELL CLONES HAVING AN ENDOGENEOUS UROTENSIN II RECEPTOR

(75) Inventors: Lisa Minor, Flemington, NJ (US);
Jenson Qi, Chalfont, PA (US);
Yuanping Wang, Dresher, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 637 days.

(21) Appl. No.: 11/501,559

(22) Filed: Aug. 9, 2006

(65) Prior Publication Data

US 2007/0082368 A1 Apr. 12, 2007

Related U.S. Application Data

(60) Provisional application No. 60/708,221, filed on Aug. 15, 2005.

(51) Int. Cl.
*C12N 5/10* (2006.01)
(52) U.S. Cl. ...................................... 435/325
(58) Field of Classification Search ................ None
See application file for complete search history.

(56) References Cited

U.S. PATENT DOCUMENTS 5,223,409 A 6/1993 Ladner
5,571,698 A 11/1996 Ladner

FOREIGN PATENT DOCUMENTS

WO WO 2006/012470 A 11/2006

OTHER PUBLICATIONS

Ames R.S. et al.: Human Urotensin-II is a Potent Vasoconstrictor and Agonist for the Orphan Receptor GPR14 Nature, Nature Publishing Group, London, GB, vol. 401, Sep. 16, 1999, pp. 282-287 XP002933799.
Douglas, S.A. et al: "From 'gills to pills': Urotensin-II as a Regulator of Mammalian Cardiorenal Function" Trends in Pharmacological Sciences, Elsevier, Amsterdam, NL, vol. 25, No. 2, Feb. 2004, pp. 76-85, XP004489198.
Douglas, Stephen A. et al.: "Identfication and Pharmacological Characterization of Native, Functional Human Urotensin-II Receptors in Rhabdomyosarcoma Cell Lines" British Journal of Pharmacology, vol. 142, No. 6, Jul. 2004, pp. 921-932 XP002418291.
Qi, J.S. et al: "Characterization of Functional Urotensin II Receptors in Human Skeletal Muscle Myoblasts: Comparison with Angiotensin II Receptors" Peptides, Elsevier, Amsterdam, US, vol. 26, No. 4, Apr. 2005, pp. 683-690, XP004773459.
Behm et al., "Differential Agonistic and Antagonistic Effects of the Urotensin-II Ligand SB-710411 at Rodent and Primate UT Receptors", European Journal of Pharmacology 492(2-3): (2004).
Coller et al., "Poisson Statistical Analysis of Repetitive Subcloning by the Limiting Dilution Technique as a Way of Assessing Hybridoma Monoclonality", Methods in Enzymology 121:412-417 (1986).
Coulouarn et al., "Cloning Sequence Analysis and Tissue Distribution of the Mouse Rat Urotensin II Precursors", FEBS Lett. 457(1): 28-32 (1999).
Cull et al., "Screening for Receptor Ligands Using Large Libraries of Peptides Linked to the C Terminus of the Lac Receptor", Proc. Natl. Acad. Sci. USA 89: 1865-1869 (1992).
Douglas et al., "Differential Vasoconstrictor Activity of Human Urotensin-II in Vascular Tissue Isolated from the Rat, Mouse, Dog, Pig, Marmoset and Cynomolgus Monkey", 131(7):1262-74, (2000).
Fodor, "Multiplexed Biochemical Assays with Biological Chips", Nature364(6437): 555-556 (1993).
Gardiner et al., "Depressor and Regionally-Selective Vasodilator Effects of Human and Rat Urotensin II in Conscious Rats", British Journal of Pharmacology 132(8): 1625-1629 (2001).
Gardiner, "Bolus Injection of Human UII in Conscious Rats Evokes a Biphasic Haemodynamic Response", British Journal of Pharmacology 143(3): 422-30 (2004).
Hassan, "Effect of Human Urotensin-II Infusion on Hemodynamics and Cardiac Function", Canadian Journal of Physiology and Pharmacology 81(2): 125-128 (2003).
Houghten, "The Use of Synthetic Peptide Combinatorial Libraries for the Identification of Bioactive Peptides", BioTechniques 13(3): 412-421(1992).
Lam, "A New Type of Synthetic Peptide Library for Identifying Ligand-Binding Activity", Nature 354(6348): (1991).
Lam, "Application of combinatorial library methods in cancer research and drug discovery", Anti-Cancer Drug Design, 12:145-167 (1997).
Lin et al., "Central Cardiovascular Action of Urotensin II in Conscious Rats", Journal of Hypertension 21(1): 159-165 (2003).
Minta et al., "Fluorescent Indicators for Cytosolic Calcium Based on Rhodamine and Fluorescein Chromophores", The Journal of Biological Chemistry 264(14): 8171-8178 (1989).
Monteith and Bird, "Techniques: High-throughput measurement of intracellular $^{Ca2+}$ - back to basics", Trends in Pharmacological Sciences 26(4): 218-223 (2005).
Russell, "Emerging Roles of Urotensin II in Cardiovascular Disease", Pharmacology and Therapeutics 103:223-243 (2004).
Scott and Smith, "Searching for Peptide Ligands with an Epitope Library", Science 249(4967):386-390 (1990).
Staszewski, "Cloning by Limiting Dilution: an improved Estimate that an Interesting Culture is Monoclonal", Yale Journal of Biology and Medicine 57(6): 865-868 (1984).

(Continued)

Primary Examiner—Michael Pak

(57) ABSTRACT

Human cell clones with increased specific binding to urotensin II have been sub-cloned from SJRH30 (ATCC® Number: CRL-2061™). These cell clones have been used for functional analyses of the biological activity of an endogeneous urotensin II receptor, as well as for identifying compounds that regulate the biological activity of an Urotensin II receptor.

10 Claims, 10 Drawing Sheets

OTHER PUBLICATIONS

Sugo et al., "Identification of urotensin II-related peptide as the urotensin II-immunoreactive molecule in rat brain," Biochemical and Biophysical Research Communications 310:860-868 (2003).

Zuckermann et al., "Discovery of Nanomolar Ligands for 7-Transmembran G-Protein_coupled Receptors from a Diverse N-(Substituted)glycine Peptoid Library", Journal of Medicinal Chemistry 37:2678-2685 (1994).

1A

1B

1C

1D

Figure 2A. Specific binding of $^{125}$I-human UII to RMS13 cells.

Kd = 0.245 nM

Based on the number of cells in a well and Bmax value, the number of UT receptors in RMS13 was 3525 receptors/cell.

Figure 2B. Specific binding of $^{125}$I-human UII to 6D9 cells.
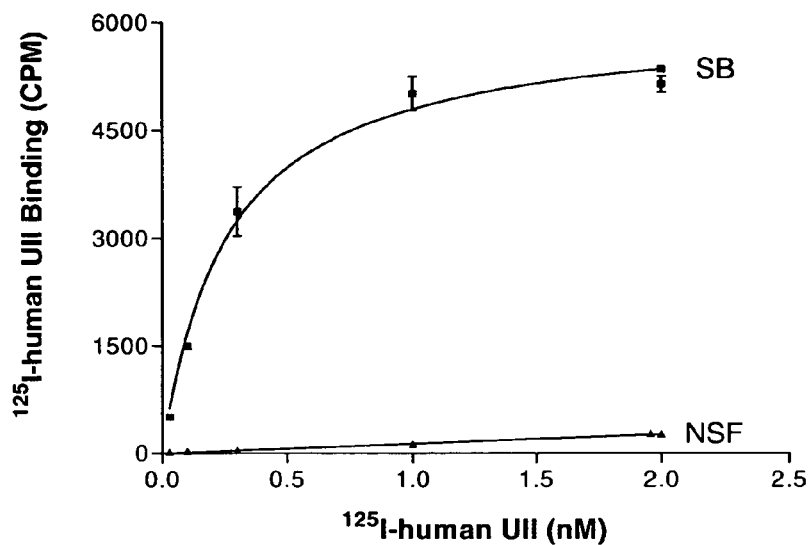
Kd = 0.259 nM.
Based on the number of cells in a well and Bmax value, the number of UT receptors in RMS13 was 6832 receptors/cell (n=2). 6253 in this experiment.

A.

B.

HUMAN CELL CLONES HAVING AN ENDOGENEOUS UROTENSIN II RECEPTOR

CROSS REFERENCE TO RELATED APPLICATIONS

This application claims priority to Application No. 60/708,221 filed on Aug. 15, 2005, the entire contents of which are incorporated by reference herein.

FIELD OF INVENTION

The present invention relates to human cell clones and methods of using the cell clones. Particularly, the present invention relates to human cell clones that are useful for functional analyses of the biological activity of an endogeneous urotensin II receptor, and their use in identifying compounds that regulate the biological activity of an Urotensin II receptor.

BACKGROUND OF THE INVENTION

Urotensin II is a somatosatin-like cyclized peptide that is conserved across many species including fish, frog, mouse, rat, pig, and human (Coulouarn et al., 1999, *FEBS. Lett.* 457(1): 28-32). G-protein-coupled receptor 14 (GPR14), also known as sensory epithelium neuropeptide-like receptor (SENR), was recently identified as to function as an U-II receptor (UT receptor, Ames et al., 1999, *Nature* 401(6750): 282-6). Human U-II binds to recombinant human GPR14 with high affinity and the binding is functionally coupled to calcium mobilization.

Emerging roles of U-II in cardiovascular diseases have been implicated (Russell, 2004, *Pharmcology & Therapeutics* 103: 223-243). Recent evidence suggests that the UT receptor system is up-regulated in multi-organ disease states, such as congestive heart failure (CHF), pulmonary hypertension, and chronic renal failure. A number of non-peptide UT receptor antagonists have been developed with the aim of dampening harmful effects of over-activated UT receptors (see, i.e., Douglas et al, 2004, *Trends Pharmacol Sci.* 25: 76-85). However, U-II exhibits significant species differences, as well as regional and functional differences between vessels (Douglas et al., 2000, *Br. J. Pharmacol.* 131(7): 1262-74). Molecules identified as antagonists for the rat receptor can behave as agonists against the monkey receptor (Behm, et al., 2004, *European Journal of Pharmacology* 492(2-3): 113-116). Thus, it is critical to confirm the effect of a putative drug-like molecule on the biological activities of an endogeneous human UT receptor in a cellular functional assay.

Until recently, there lacked a suitable human cell line for studying the biological activities of an endogeneous UT receptor. U-II binding or calcium mobilization coupled to U-II receptor activation has been detected in very few native cell lines. In 2004, Qi reported that primary human skeletal muscle myoblasts bind U-II. In addition, they reported that the primary human skeletal muscle myoblasts had a slight but significant calcium mobilization in response to U-II (Qi, et al., 2005, *Peptides,* 26(4):683-690). Douglas et al. (2004, *Br. J. Pharmacol.* 142(6): 921-32) reported that an appreciable human U-II binding site density was observed in a human skeletal muscle rhabdomyosarcoma cell, SJRH30 (ATCC® Number: CRL-2061™, also named RC13, or RMS 13). However, they also observed that "only ~10% SJRH30 cells exposed to hU-II responded with an appreciable $[Ca^{2+}]_i$ response," and "the magnitude of the hU-II-induced $[Ca^{2+}]_i$ varied significantly between individual cells from ~10 nM to several hundred nM over baseline." The calcium mobilization coupled to U-II receptor activation in SJRH30 is not robust enough for high throughput screening of compounds that increase or decrease the biological activity of U-II receptor.

To facilitate the development of new compounds that regulate the biological activity of UT receptor, there is a need to establish a human cell clone that allows robust and simple measurement of the ability of a candidate compound to increase or decrease the biological activity of an endogeneous UT receptor in the cell.

SUMMARY OF THE INVENTION

Human cell clones are now obtained that have increased number of endogeneous urotensin II binding sites per cell. The cell clones have been used for identifying compounds that regulate the biological activity of the UT receptor.

Thus, one general aspect of the invention is a human cell clone that is a sub-clone of SJRH30 (ATCC® Number: CRL-2061™), having at least about 50% more endogeneous urotensin II binding sites cell$^{-1}$ than those of the parental SJRH30. The invention provides a cell culture comprising cells of a human cell clone that is a sub-clone of SJRH30 (ATCC® Number: CRL-2061™), having at least about 50% more endogeneous urotensin II binding sites cells$^{-1}$ than those of the parental SJRH30.

Another general aspect of the invention is a method of identifying a compound that increases the biological activity of an urotensin II receptor, comprising the steps of: a) administering a test compound in a buffer solution to a cell culture comprising cells of a human cell clone that is a sub-clone of SJRH30 (ATCC® Number: CRL-2061™), said cell culture having at least about 50% more endogeneous urotensin II binding sites cells$^{-1}$ than those of the parental SJRH30; b) measuring the biological activity of the urotensin II receptor of the cells in the cell culture; c) repeating steps a) and b), but omitting the test compound from the buffer solution; and d) comparing the result obtained from step b) with that from step c).

The invention also provides a method of identifying a compound that decreases the biological activity of an urotensin II receptor, comprising the steps of: a) administering a test compound in a buffer solution to a cell culture comprising cells of a human cell clone that is a sub-clone of SJRH30 (ATCC® Number: CRL-2061™), said cell culture having at least about 50% more endogeneous urotensin II binding sites cells$^{-1}$ than those of the parental SJRH30; b) administering an urotensin II or a functional equivalent thereof to the cell culture; c) measuring the biological activity of the urotensin II receptor of the cells in the cell culture; d) repeating steps a), b), and c), omitting the test compound from the buffer solution; and e) comparing the result obtained from step c) with that from step d).

In particular embodiments of methods of the invention, the step of measuring the biological activity of the urotensin II receptor comprises measuring calcium mobilization in the cells.

The invention further provides a method of identifying a compound that binds to an endogeneous urotensin II binding site, comprising the steps of: a) administering a test compound in a buffer solution to a cell culture comprising cells of a human cell clone that is a sub-clone of SJRH30 (ATCC® Number: CRL-2061™), said cell culture having at least about 50% more endogeneous urotensin II binding sites cell$^{-1}$ than those of the parental SJRH30; and b) measuring the amount of the test compound bound to the endogeneous urotensin H binding sites of the cells in the cell culture.

BRIEF DESCRIPTION OF THE DRAWINGS

FIGS. 2A and 2B show that the 6D9 cells had more specific binding to hU-II than the SJRH30 (RMS-13) cells: filled square—specific binding of hU-II to 6D9 cells; filled square—specific binding of hU-II to SJRH30 (RMS-13) cells; filled triangle—nonspecific binding of hU-II to 6D9 cells; and filled triangle—nonspecific binding of hU-II to SJRH30 (RMS-13) cells.

DETAILED DESCRIPTION OF THE INVENTION

Figure 1:
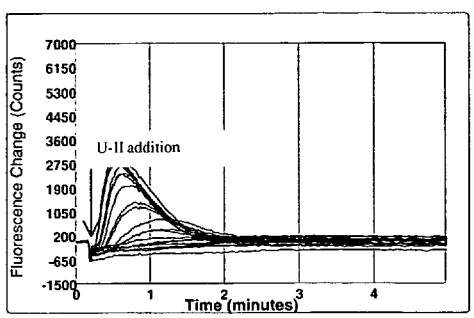
FIG. 1 illustrates that three sub-clones of SJRH30, 10A7, 6D9, and 4G5, more efficiently mobilized calcium in response to U-II, as compared to SJRH30. U-II was added at the 10 second interval in concentrations ranging from 0 to 100 nM: 1A—multiple well overlay plot of 10A7; 1B—multiple well overlay plot of 6D9; 1C—multiple well overlay plot of 4G5; and 1D—multiple well overlay plot of SJRH30.
Figure 1:
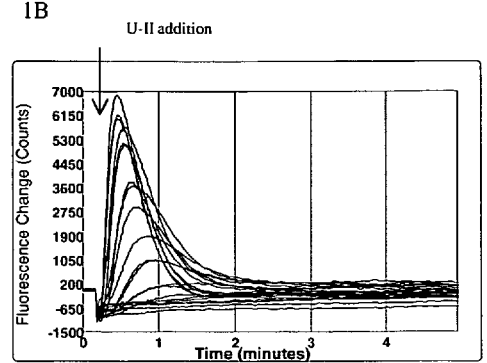
Figure 1:
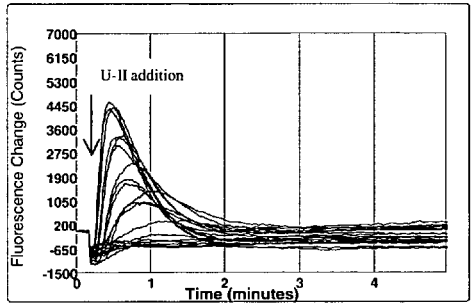
Figure 1:
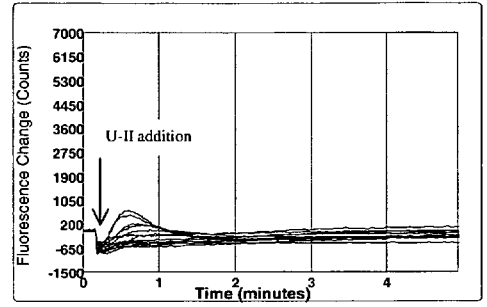

All publications cited herein after are hereby incorporated by reference. Unless defined otherwise, all technical and scientific terms used herein have the same meaning as commonly understood to one of ordinary skill in the art to which this invention pertains.

It must be noted that as used herein and in the appended claims, the singular forms "a," "an," and "the" include plural reference unless the context clearly dictates otherwise. Thus, for example, a reference to "a cell" is a reference to one or more cells and includes equivalents thereof known to those skilled in the art and so forth.

As used herein, the terms "comprising", "containing", "having" and "including" are used in their open, non-limiting sense.

The following are some abbreviations that are at times used in this specification:
ATCC=American Type Culture Collection
CPM=count per minute
FLIPR=fluorescence imaging plate reader
GPCR=G protein coupled receptor
HTS=high throughput screening
hU-II=human Urotensin-II
PBS=phosphate buffer saline
U-II=Urotensin-II
URP=Urotensin-II-related peptide
UT receptor=Urotensin-II receptor As used herein, a "cell clone" refers to a population of cells derived from a single common ancestral cell by mitosis in eukaryotes, such as a human cell clone, or by binary fission in prokaryotes. Although cells within a cell clone are presumed to be genetically identical, mutational events may abrogate the genetic homogeneity.

As used herein, "sub-clone" is a process whereby a cell clone is obtained from one or few ancestral cells of a parental cell clone. In a particular embodiment, cells within the sub-cloned cell clone have less genetic variability to one to another than cells within the parental cell clone. Depending on the context, "sub-clone" can also refer to the cell clone resulting from the sub-cloning process. To ensure genetic stability, the clone is frozen in early passage and cultures replaced with the frozen stocks at regular intervals.

As used herein, "urotensin-II", "U-II", or "U2", used interchangeably herein, each refers to a peptide having a conserved cyclic hexapeptide, SEQ ID NO: 1, CFWKYC, wherein an intramolecular disulfide bond was formed between the two cysteines of the hexapeptide. Examples of "urotensin-II" include, but are not limited to, those listed in Table 1, with an intramolecular disulfide bond between the two cysteines of the hexapeptide of SEQ ID NO: 1. "Urotensin-II" also includes the so-called U-II-related peptide (URP), for example, consisting essentially of SEQ ID NO: 10, ACFWKYCV, with an intramolecular disulfide bond formed between the two cysteines (Sugo et al., 2003, *Biochem Biophys Res Commun* 2003; 310:860-8). An "urotensin-II" can be isolated from a natural source, such as an U-II producing animal. An "urotensin-II" can also be synthesized via any in vitro method, such as an in vitro peptide synthesis reaction.

TABLE 1

Examples of urotensin-II from various species

| Species | Sequence of urotensin-II |
|---|---|
| Human | SEQ ID NO: 2, ETPDCFWKYCV |
| Frog | SEQ ID NO: 3, AGNLSECFWKYCV |
| Trout | SEQ ID NO: 4, GGNSECFWKYCV |
| Carp α | SEQ ID NO: 5, GGGAECFWKYCV |
| Porcine - 1 | SEQ ID NO: 6, GTPSECFWKYCV |
| Porcine - 2 | SEQ ID NO: 7, GPPSECFWKYCV |
| Rat - 1 | SEQ ID NO: 8, HGTAPECFWKYCI |
| Mouse | SEQ ID NO: 9, HGAAPECFWKYCI |

A "functional equivalent of urotensin-II" is a chemical entity that has all or part of the biological activity of urotensin-II, i.e., to bind to an urotensin-II receptor, and the binding can be functionally coupled to calcium mobilization. Examples of "functional equivalent of urotensin-II" include, but are not limited to, modifications or truncations of urotensin-II, or fusion proteins comprising urotensin-II, that maintain all or part of the biological activities of an urotensin-II. "Functional equivalent of urotensin-II" also includes, but are not limited, to the non-peptide U-II mimetics, non-peptide UT receptor agonists, inverse agonists or antagonists. The "functional equivalent of urotensin-II" can be from either natural or non-natural sources. Non-natural sources include, for example, recombinant or synthetic sources.

As used herein, an "urotensin II receptor", "U-II receptor", "UTR2", "UT receptor" or "U2R", used interchangeably herein, each refers to a G-protein-coupled receptor protein that binds to an urotensin II (U-II) or an analog thereof, and the binding can be functionally coupled to calcium mobilization. An "urotensin II receptor", can (1) have greater than about 60% amino acid sequence identity to a human U-II receptor (NCBI protein accession number: NP_061822); (2) bind to antibodies, e.g., polyclonal or monoclonal antibodies, raised against a human U-II receptor (NCBI protein accession number: NP_061822); or (3) be encoded by a polynucleotide that specifically hybridizes under stringent hybridization conditions to a nucleic acid molecule having a sequence that has greater than about 60% nucleotide sequence identity to the coding region of a human U-II receptor cDNA (NCBI nucleotide accession number: NM_018949).

"Stringent hybridization conditions" has the meaning known in the art, as described in Sambrook et al., *Molecular Cloning: A Laboratory Manual*, Second Edition, Cold Spring Harbor Laboratory, Cold Spring Harbor, New York, (1989). An exemplary stringent hybridization condition comprises hybridization in 6× sodium chloride/sodium citrate (SSC) at about 45° C., followed by one or more washes in 0.2×SSC and 0.1% SDS at 50-65° C.

In some embodiments, the "U-II receptor" has greater than about 65, 70, 75, 80, 85, 90, or 95 percent amino acid sequence identity to a human U-II receptor (NCBI protein accession number: NP_061822). Exemplary U-II receptor includes human U-II receptor, which includes structural and functional polymorphisms of the human U-II receptor depicted in NCBI protein accession number: NP_061822. "Polymorphism" refers to a set of genetic variants at a particular genetic locus among individuals in a population. U-II receptor also includes orthologs of the human U-II receptor in other animals such as rat (i.e., NCBI protein accession NO: NP_065412), mouse (i.e., NCBI protein accession NO: NP_663415), pig, dog and monkey.

An "endogeneous urotensin II binding site" refers to a site on which an urotensin II can specifically bind to, and the site is naturally produced by or associated with the cell. "Naturally" in this context means that the U-II binding site is not recombinantly made, i.e., not genetically altered or modified by artificial means. In one embodiment, an endogeneous urotensin II binding site is found on an endogeneous urotensin II receptor. The number of the endogeneous urotensin II binding sites of a cell can be calculated using any methods known to a person skilled in the art. In one embodiment, the number of endogeneous urotensin II binding sites of a cell can be calculated from the U-II receptor-ligand binding curve resulting from an U-II receptor-binding assay. Example 2 (infra) describes a specific example of how to measure and calculate the number of endogeneous urotensin II binding sites per cell.

As used herein, the "biological activity of an urotensin II receptor" refers to an activity exerted by the urotensin II receptor as determined in vivo, or in vitro, according to standard techniques. Such an activity can be a direct activity such as the ability of an urotensin II receptor to bind to an urotensin II (U-II) or an analog thereof, and the binding can be functionally coupled to calcium mobilization. A biological activity of an urotensin II receptor can also be an indirect activity, such as a signal transduction activity mediated by the urotensin II receptor via its interaction with one or more than one additional protein or other molecule(s), including but not limited to, interactions that occur in a multi-step, serial fashion. For example, an urotensin II receptor has the biological activity of mediating the function of U-II or a functional derivative thereof as an endothelium independent vasoconstrictor or an endothelium dependent vasodilator.

A "signal transduction" is the cascade of processes by which an extracellular signal interacts with a receptor at a cell surface, causing a change in the level of a second messenger, and ultimately effects a change in the cell function.

A "signal transduction activity mediated by urotensin II receptor" refers to a signal transduction, wherein the extracellular signal is urotensin II or a functional equivalent thereof. In one embodiment, a "signal transduction activity mediated by urotensin II receptor" is the cascade of processes by which urotensin II binds to an urotensin II receptor at a cell surface, causing a change in the level of a second messenger, such as calcium or cyclic AMP, and ultimately effects a change in the cell's function. The change in the cell's function can be the change of any cellular process urotensin II is involved in. Changes in the cell's function often lead to changes of the animal physiology. For example, a "signal transduction activity mediated by urotensin II receptor" can be an endothelium independent vasoconstriction or an endothelium dependent vasodilation triggered by urotensin II.

As used herein, "calcium mobilization" refers to the process whereby the concentration of intracellular free $Ca^{2+}$, also denoted $[Ca^{2+}]_i$, increases or decreases during signal transduction. $[Ca^{2+}]_i$ increases due to, for example, release of $Ca^{2+}$ from internal storage, or increased influx of $Ca^{2+}$ across the plasma membrane and into the cell.

As described herein, a "test molecule", "test compound", or "candidate compound", used interchangeably herein, each means a molecule that is subjected to the assay systems and methods described herein. Test compounds or candidate compounds encompass numerous chemical classes, although typically they are organic compounds. Preferably, they are small organic compounds, i.e., those having a molecular weight of more than 50 Kd yet less than about 2500 Kd. Candidate compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated.

Candidate compounds can be obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including: biological libraries; spatially addressable parallel solid phase or solution phase libraries: synthetic library methods requiring deconvolution; the "one-bead one-compound" library method; and synthetic library methods using affinity chromatography selection (Lam (1997) *Anticancer Drug Des.* 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents can be subjected to directed or random chemical modifications such as acylation, alkylation, esterification, amidation, etc. to produce structural analogs of the agents. Candidate compounds can be selected randomly or can be based on existing compounds that bind to and/or modulate the function of chloride channel activity. Therefore, a source of candidate agents is libraries of molecules based on a known compound that increases or decreases the biological activity of a U-II receptor, in which the structure of the known compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries.

A variety of other reagents also can be included in the method. These include reagents such as salts, buffers, neutral proteins (e.g., albumin), detergents, etc. Other reagents that improve the efficiency of the assay such as nuclease inhibitors, antimicrobial agents, and the like can also be used.

Examples of methods for the synthesis of molecular libraries can be found in the art, for example in: Zuckermann et al. (1994). *J Med. Chem.* 37:2678. Libraries of compounds can be presented in solution (e.g., Houghten (1992) *Biotechniques* 13:412-421), or on beads (Lam (1991) *Nature* 354:82-84), chips (Fodor (1993) Nature 364:555-556), bacteria (U.S. Pat. No. 5,223,409), spores (U.S. Pat. No. 5,571,698), plasmids (Cull et al. (1992) *Proc. Natl. Acad. Sci*. USA 89:1865-1869) or phage (see e.g., Scott and Smith (1990) *Science* 249:3 86-390).

The term "high throughput" refers to an assay design that allows easy screening of multiple samples simultaneously, and provides a capacity for robotic manipulation. Another desired feature of high throughput assays is an assay design that is optimized to reduce reagent usage, or minimize the number of manipulations in order to achieve the analysis desired. Examples of high throughput assay formats include 96-well or 384-well plates, levitating droplets, and "lab on a chip" microchannel chips used for liquid handling experiments.

One general aspect of the invention is a human cell clone that has increased endogenous urotensin II binding sites, enabling robust and efficient functional analyses of the biological activity of endogenous UT receptor in the cell clone. The invention provides a human cell clone that is a sub-clone of SJRH30 (ATCC® Number: CRL-2061™), having at least about 50% more endogenous urotensin II binding sites cell$^{-1}$ than those of the parental SJRH30. The invention further provides a cell culture comprising cells of a human cell clone that is a sub-clone of SJRH30 (ATCC® Number: CRL-2061™), having at least about 50% more endogenous urotensin II binding sites cells$^{-1}$ than those of the parental SJRH30.

In particular embodiments, the cell clones of the invention have at least about 100%, 150%, 200%, 250%, 300%, 350%, 400%, 450%, 500% or 550% or more endogenous urotensin II binding sites cell$^{-1}$ than those of the parental SJRH30. For example, the cell clones of the invention can be a sub-clone of SJRH30 selected from 6D9 (ATCC® Number: PTA-7749), 4G5 (ATCC® Number: PTA-7747), or 10A7 (ATCC® Number: PTA-7748), which has endogenous urotensin II binding sites cell$^{-1}$ that are about 5.2 fold, 2.7 fold, or 3.3 fold, respectively, of those of the parental SJRH30.

The cells of the invention exhibited an increase in the amount of U-II receptor mRNA as well as an increase in total receptor binding to U-II. Thus, the biological activity of an endogenous U-II receptor can be detected more robustly from the cells of the invention as compared to prior known cells. For the first time, the present invention enabled a HTS screening of the biological activity of an endogenous U-II receptor in a cellular assay.

Thus, the present invention provides methods of using the human cell clone of the invention to identify compounds that increase or decrease the biological activity of an urotensin II receptor. The inventive assay methods can be used to detect test compounds that increase or decrease the biological activity of an U-II receptor in any manner. Compounds that increase or decrease the biological activity of an U-II receptor can be compounds that interact directly with the U-II receptor in such a way as to affect the biological activity of U-II receptor. For example, such a compound can bind to the U-II receptor and affect the interaction of the receptor with U-II or other protein/molecule, such as a functional derivative of U-II, i.e., an U-II mimetic, an agonist or antagonist of U-II. Compounds that increase or decrease the biological activity of an U-II receptor can also be compounds that interact indirectly with the U-II receptor in such a way as to affect the biological activity of U-II receptor. For example, such a compound can bind to protein(s) or molecules other than the U-II receptor, and affect the signal transduction activity of the U-II receptor.

In a method of identifying a compound that increases the biological activity of an urotensin II receptor, a test compound in a buffer is administered to cells of a human cell clone of the invention. The biological activity of the urotensin II receptor of the cells can be measured, and compared to that of a control wherein the buffer rather than the test compound is administered to the cells. The test compound that increases the biological activity of the U-II receptor can thus be identified and subject to further analyses.

In a method of identifying a compound that decreases a biological activity of an urotensin II receptor, cells of a human cell clone of the invention are exposed to a test compound and are exposed to a compound that is known to activate the U-II receptor. The cells can be exposed to the test compound either before, after, or simultaneously with the exposure of the cells to the compound that is known to activate the U-II receptor. The biological activity of the urotensin II receptor of the cells can be measured, and compared to that of a control wherein the cells are exposed to the U-II receptor activating compound only, not the test compound. The test compound that inhibits the biological activity of the U-II receptor can thus be identified and subject to further analyses.

The biological activity of the urotensin H receptor can be measured using means known to a person skilled in the art. For example, it can be measured for the ability of the U-II receptor to bind to a U-II, a functional derivative of U-II, or any other compound that is known to bind to the receptor. The biological activity of the U-II receptor can also be measured by monitoring calcium mobilization. Activation of the U-II receptor is coupled with an increase in $[Ca^{2+}]_i$. It has become common to follow changes in $[Ca^{2+}]_i$ in cell populations or even single cells, as a function of time, with the recent development of calcium-sensitive fluorescent dyes, such as quin-2, fura-2, and indo-1 (Minta et al., 1989, *J Biol Chem.* 264(14): 8171-8 and references therein). High-throughput technologies have been developed and used to measure $[Ca^{2+}]_i$ (see review Monteith and Bird, 2005, *Trends in Pharmacological*

*Sciences*, 26: 218-223). For example, the high-throughput approach using FLIPR® enables the simultaneous measurement of $Ca^{2+}$ signals in microplates with 96-, 384-, and 1536-well formats in the time normally taken to complete one measurement using previous techniques.

The methods of the invention can be combined with other means of testing a compound for its ability to increase or decrease the U-II receptor's biological activity. For example, compounds that increase or decrease the U-II receptor's biological activity can be further tested in an animal model for its ability to cause changes in animal physiology. For example, it was observed that administering U-II to a rat induced an increase in the redness or skin temperature of the rat ear (Qi et al., U.S. patent application Ser. No. 60/680,449, filed May 12, 2005; a systemic administration of human U-II to anethetized monkeys resulted in a decrease in total peripheral conductance and cardiac contractility (Ames, 1999, supra); intravenous bolus injection of U-II into anethetized rats produced a decrease in mean arterial pressure, left ventricular systolic pressure and cardiac contractility (Hassan, 2003, *Can J Physiol Pharmacol* 81(2): 125-8); bolus injection of U-II to conscious rats evokes an initial response consisting of tachycardia and hypotension, followed by a later phase (30-120 min post injection) of tachycardia and hypertension (Gardiner, 2004, *Br J Pharmacol* 143(3): 422-30); indomethacin and L-NAME together prevented both phases of the haemodynamic responses to U-II (Gardiner, 2004, supra); and in conscious rats the predominant hemodynamic effect of U-II is systemic vasodilatation with dose-dependent tachycardia (Gardiner, 2001 et al., *Br J Pharmacol* 132(8): 1625-9; and Lin et al, 2003, *J Hypertens* 21(1): 159-65).

This invention will be better understood by reference to the examples that follow. Those skilled in the art will readily appreciate that these examples are only illustrative of the invention as described more fully in the claims that follow thereafter.

Example 1

Sub-clones of SJRH30 Having Increased Calcium Mobilization Upon U-II Activation

Dilution subcloning (Staszewski, 1984, Yale journal of biology and medicine, 57(6): 865-8; Coller et al., 1986, *Methods in enzymology* 121: 412-7) and calcium mobilization assay were used to obtain a cell clone that mobilizes calcium more efficiently in response to U-II.

The parental SJRH30 cell line (ATCC NO: CRL-2061™) and RPMI 1640 culture media (ATCC 30-2001) were obtained from ATCC (Manassas, Va.). FBS (Cat. No. SH30070.03) was from Hyclone (Logan, Utah). The Calcium 3 dye (Cat. No. R7182) was from Molecular Devices (Sonnyvale, Calif.). Probenecid (Cat. No. P-8761) and human urotensin II (Cat. No. U-7257) were from Sigma (St Louis, Mo.). Urantide was purchased from Peptide International (Cat. No. PUT-3639-P1, Louisville, Ky.). Branched DNA kits and probes were from Genospectra (Freemont, Calif.).

Unless otherwise indicated, cells of SJRH30 and its subclones were cultured in RPMI medium containing 10% FBS. Cells were split at a 1:5 to 1:10 ratio two times per week by enzyme dissociation. In this process, cells are rinsed with calcium and magnesium free PBS, a trypsin solution is added and the cells incubated until they have released from the bottom of the flask. At this time, cells are triturated, and a portion transferred to a new flask containing fresh medium.

Calcium mobilization was performed using FLIPR and Calcium 3, a non-wash $Ca^{2+}$ dye. Unlike the conventional $Ca^{2+}$ dye such as Fluo-3, Fluo-4, and Fura-2/AM, etc., the non-wash $Ca^{2+}$ dye was formulated to incorporate extracellular fluorescence quenchers and avoid the need to wash away extracellular $Ca^{2+}$ dye after loading the cells with the dye (Monteith and Bird, 2005, supra).

Cells were plated into 96 or 384 well plates and were incubated at 37° C. After the incubation, the growth medium was removed and replaced with HBSS (Hanks Balanced salt solution #21-023-CV, Mediatech, Inc, Herndon, Va.) containing Calcium 3 dye with probenecid. Probenecid concentrations were 1.25 mM, ½ the standard concentration suggested by the manufacturer unless otherwise indicated.

SJRH30 cells were trypsinized as described above and diluted to a concentration of 1 cell/100 ul volume in RPMI (10% FBS). Cells were plated at 100 ul/well into 10×96 well culture plates. After the cells were grown for 1-2 weeks on the 96-well culture plates, the replicate plates were made by washing the cells with Ca/Mg free PBS (Mediatech), adding trypsin to the washed cells (Gibco, Grand Island, N.Y.) and incubating the cells for 5 minutes, then triturating, i.e., pipeting up and down, the cells and placing 10 ul of the cells into 200 ul growth medium in separate black clear bottom 96 well plates. After about 1 week incubation of the black clear bottom 96 well plates, the wells of the plates were inspected for the presence of cell colonies. The ability of the cells to mobilize calcium in response to U-II was determined using Calcium 3 and FLIPR.

SJRH30 cells responded well to dilution sub-cloning. At the about 1-cell/100 ul volume, approximately 59% of the wells contained colonies. The wells contained cells of various morphologies; spindly, elongated and epithelium like highlighting the heterogeneous nature of the parent cell line. Cells were evaluated for response to U-II using calcium mobilization. Wells were considered positive for U-II mediated calcium mobilization if they exhibited >1000 positive Fluorescence Change when U-II (1 nM) was added. Fluorescent change is measured on a well by well basis by taking the maximum fluorescence signal and subtracting the minimal signal for each well. Using these criteria, 21.5±8.0% of the wells were found to be positive for U-II mediated calcium mobilization. Cells in a number of these wells were harvested and amplified and retested for their ability to mobilize calcium when exposed to U-II.

Cells from three wells, presumably three cell clones, were picked as being the most responsive to U-II. The three cell clones are designated 10A7, 6D9 and 4G5, all of which were deposited to the American Type Culture Collection (ATCC®) at 10801 University Boulevard, Manassas, Va. 20110 on Aug. 1, 2006. The 10A7, 6D9 and 4G5 sub-clones of SJRH30 were designed as PTA-7748, PTA-7749 and PTA-7747, respectively. All three cell clones mobilized calcium to a similar extent as did the parental SJRH30 cells when the cells were exposed to a calcium ionophore (data not shown). However, the three cell clones differed in their ability to mobilize calcium in response to U-II with 6D9>4G5>10A7>SJRH30 (FIG. 1). Under the calcium mobilization assay condition, cells of the three clones responded to U-II in a dose responsive manner, while the parental SJRH30 showed minimal to no signal (data not shown).

Figure 4:
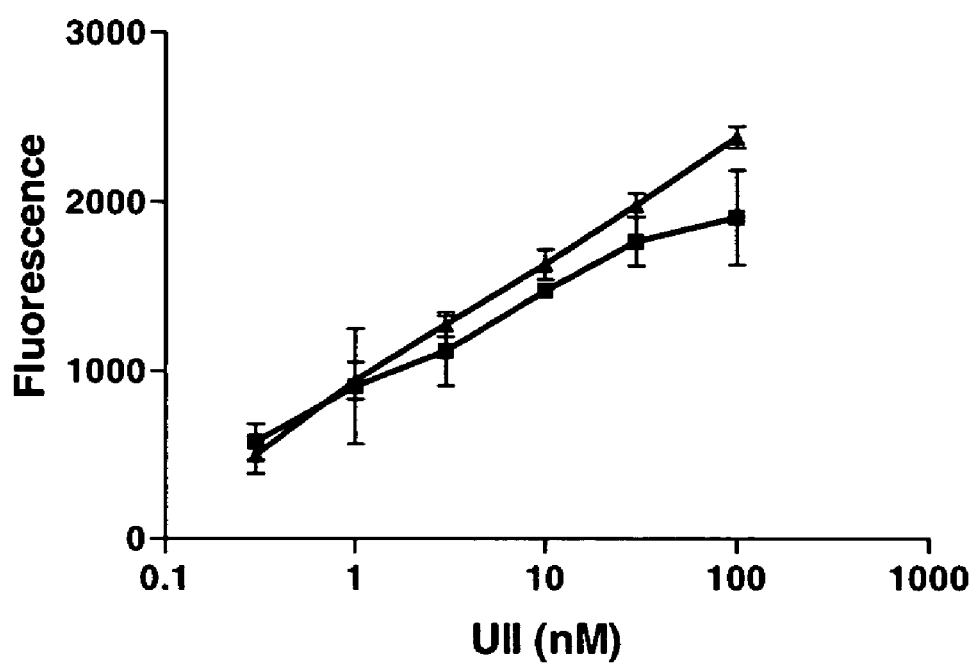
FIG. 4 shows that the 6D9 clone still responded to hU-II in a concentration dependent manner after 17 passages of the cell cultures (filled square) or following freeze-and-thawed (filled triangle).
Figure 6:
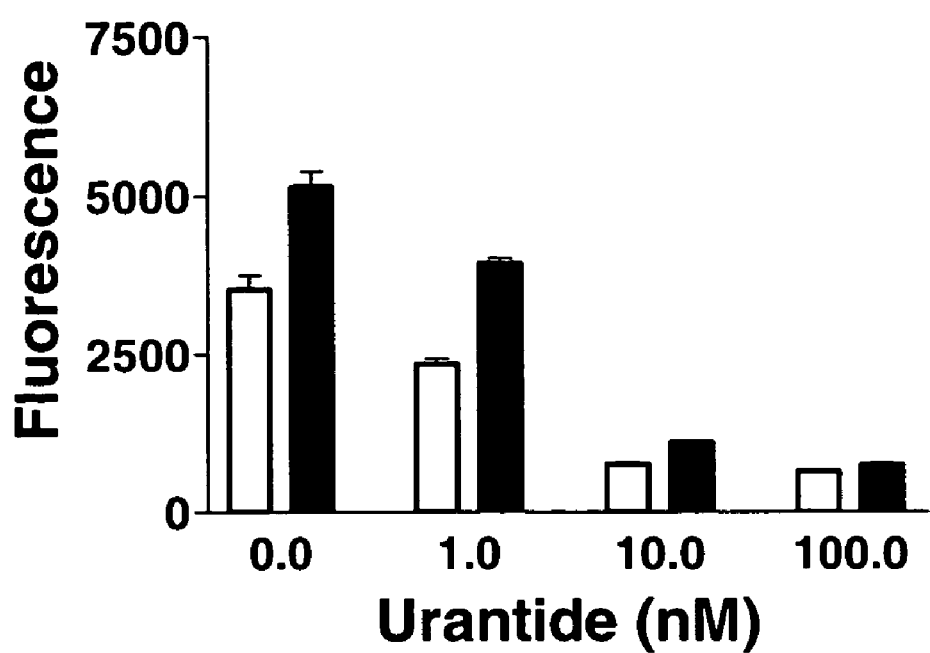
FIG. 6 shows that in the 6D9 cells, urantide, an UT receptor antagonist, blocked calcium mobilization coupled to U-II stimulation: 10 nM U-II (open bar) or 30 nM U-II (filled bar).

The U-II specific antagonist, Urantide, blocked the calcium mobilization coupled to U-II stimulation (FIG. 6), indicating that the measured calcium mobilization is indeed due to activation of U-II receptor. Newly thawed 6D9 cells responded to U-II in a similar fashion as that of the 6D9 cells prior to freezing, indicating that the cells were stable upon freezing and thawing (FIG. 4). In addition, the cells survived in cultures for over 3 months (17 passages) and were still responsive to U-II (FIG. 4).

Example 2

Sub-clones of SJRH30 Contained More Urotensin II Binding Sites

Radioligand-binding studies were performed to characterize the cell clones 6D9, 4G5, 10A7, and SJRH30.

For the [$^{125}$I]-U-II binding experiments, cells were plated in 24-well Costar plates in complete medium for 24 h to reach 60% to 80% confluence. The binding medium used was Dulbecco's modified Eagle's medium (DMEM) containing 2 mg/ml BSA and 25 mM HEPES (pH 7.4). The cells were washed at room temperature 1× with the binding medium, and were incubated with 0.1 ml per well of binding medium containing the indicated amount of [$^{125}$I]-U-II in the absence or presence of 1 μM human UII for 3 h. The cells were washed 3× with the binding medium and solubilized in 1% SDS and 0.5 N NaOH. Radioactivity was quantified by gamma counting.

Figure 2:
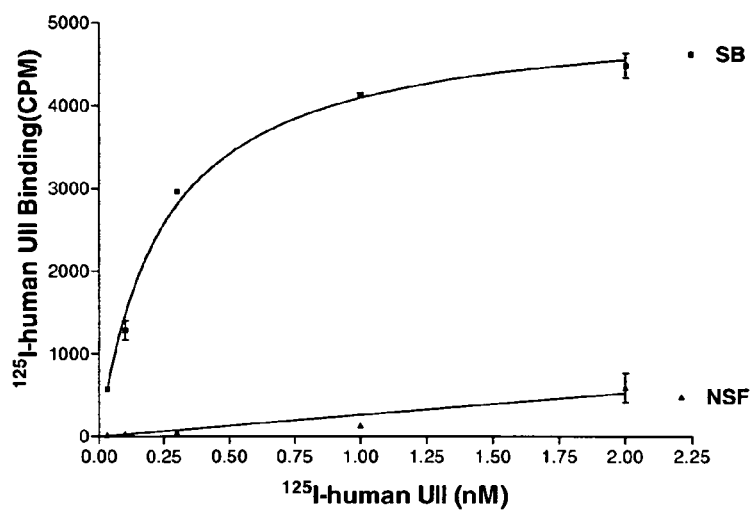
FIGS. 2A and 2B illustrate [$^{125}$ I] hU-II bound to intact cells of SJRH30 (RMS-13) cells (FIG. 2A) and the 6D9 clone (FIG. 2B) in a time-dependent manner.

Analyses of the binding curves indicates that U-II binds to cells of all three clones in a concentration dependent manner, see for example, the binding curve of 6D9 in FIG. 2B. The Kd and Bmax value of the U-II binding were determined from the binding curve. For example, SJRH30 had a Kd of 0.245 nM, and about 3525 UT binding sites/cell based on the Bmax and the number of cells in a well, while 6D9 had a Kd of 0.259 nM and about 6253 UT binding sites/cell (n=2).

Although the sub-clones contained more binding sites per cell for urotensin II than the parent (6D9 5.2 fold, 4G5 2.7 fold, 10A7 3.3 fold) the Kd for binding was identical (data not shown). This suggests that the observed increase in calcium mobilization is due to the increased U-II binding sites, not by increased binding affinity. Scatchard analysis (nonlinear regression) of the binding curves also suggested that cells of all clones interact with U-II with a single class of non-cooperative sites.

Example 3

The Sub-Cloned Human Cell Clones Have Increased Gene Expression of The UT Receptor Branched-DNA analysis was performed to measure the relative amount of mRNA of the UT receptor in the cell clones 6D9, 4G5, 10A7, and SJRH30.

In this protocol, cells are plated in 96 well plates. Cells are then lysed in the presence of pools of capture and label probes (CE and LE respectively) specific for the urotensin II receptor or for GAPDH. The lysis procedure does not require that the cellular supernatant be removed; hence this protocol works for both suspension and adherent cultures. The probes within the lysis buffer serve certain functions: CE's have complementary sequences to both the message and to a capture plate so serves to adhere the message to the plate. The LE has sequences complementary to the message as well as to the bDNA and serves as a scaffold for binding the amplifying system. Following lysis of the cells, the samples are transferred to a capture plate. The capture plate is coated with an oligonucleotide that binds the CE thus capturing the message. After hybridization, the plate is washed and the Amplifier is added (bDNA). After hybridization, the samples are washed and the label is added (DNA coupled alkaline phosphatase). The samples are hybridized, washed and the luminescent substrate, dioxetene, is added and the samples are incubated to allow the reaction to occur and the plates are read on a luminometer.

Figure 3:
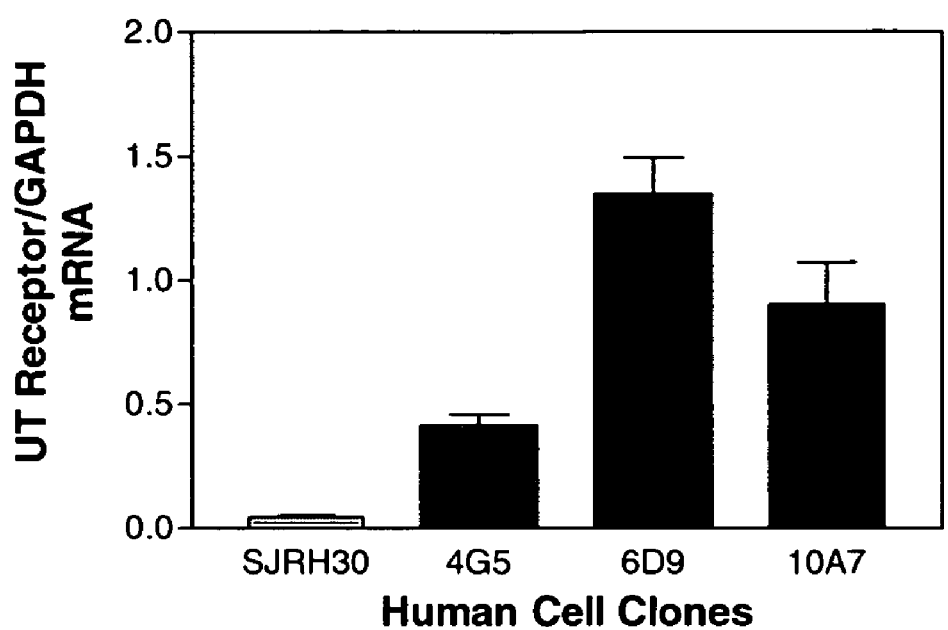
FIG. 3 shows increased gene expression of the UT receptor in human cell clones, 10A7, 6D9, and 4G5 as compared to SJRH30.

The subclones expressed increased the amount of UT receptor mRNA as compared to the SJRH30 (FIG. 3). This suggests that the increased UII binding sites of cells of the subclones are likely due to the increased expression of UII receptors of the cells.

Example 4

A High Throuhput Assay

This Example teaches a high throughput approach using FLIPR on a 384-well format. Other formats of high throughput assays can be conducted using protocols similar to this example.

Figure 5:
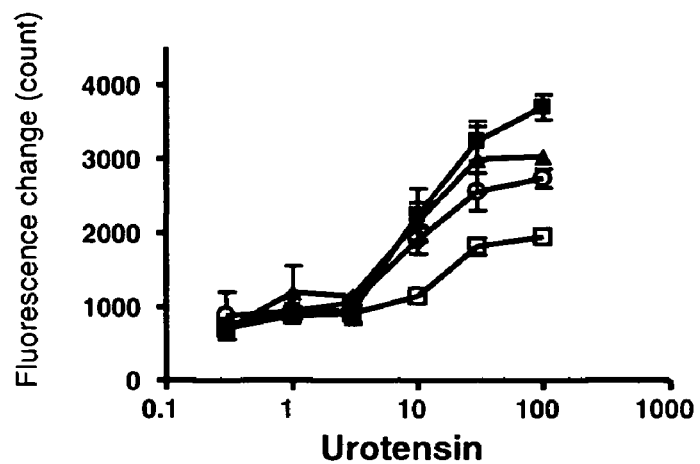
FIG. 5 illustrates the optimal 6D9 cell density for assaying the hU-II coupled calcium mobilization with a Day 1 (5A) or Day 2 (5B) cell culture: filled square—35,000 cells/well; filled triangle—30,000 cells/well; open circle—25,000 cells/well; and open square—20,000 cells/well.
Figure 5:
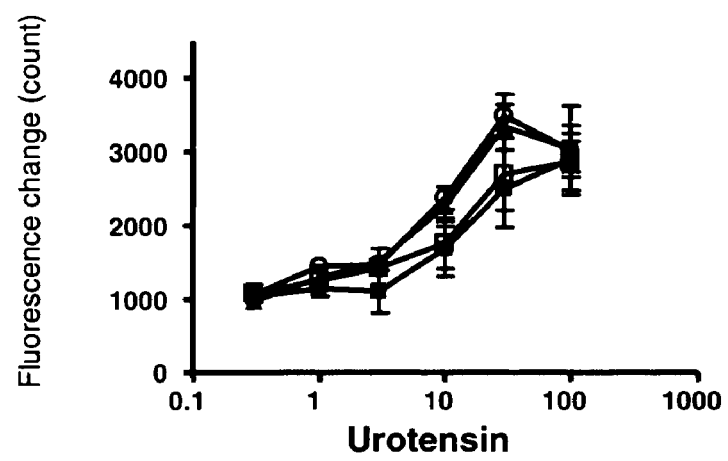

Various factors of the FLIPR assay had been tested to minimize the measure variability. For example, it was found that under the assay condition, the optimal cell density for maximal response to U-II was about 30,000 per ml after the cells were incubated in plates for either 1 or 2 days (FIG. 5). In addition, detecting the fluorescent signal of Calcium 3 between about 30-45 minutes after the dye was added to the cells appeared to decrease the variability of the assay.

Figure 7A:
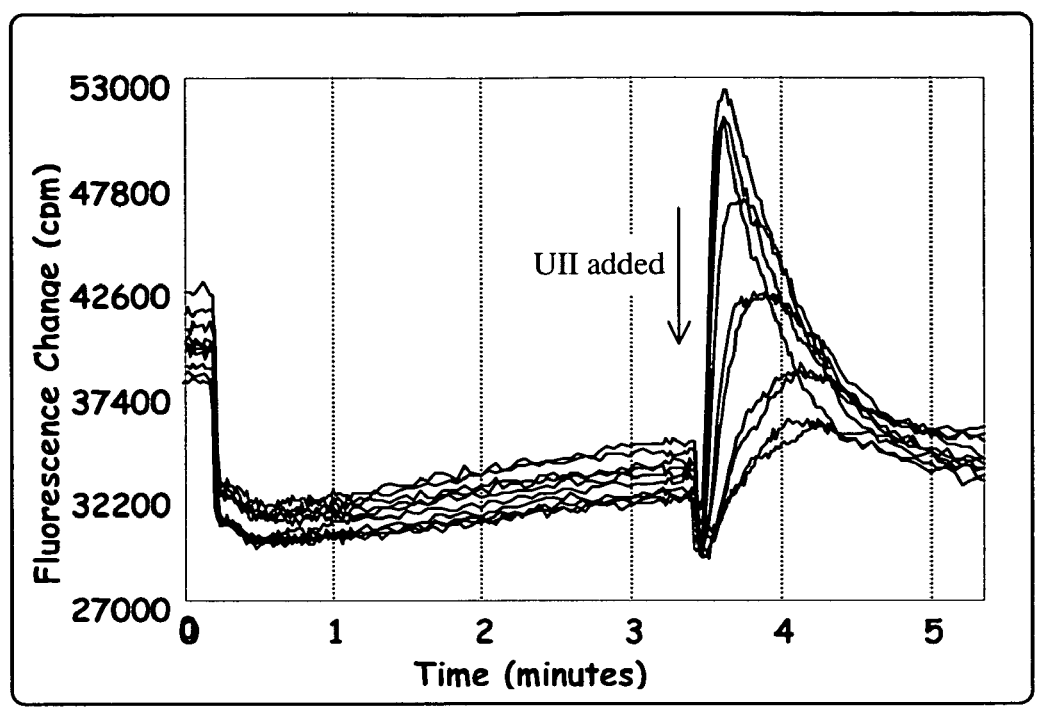
FIG. 7 illustrates consistent calcium mobilization results obtained from 6D9 cells using a 384-well FLIPR assay: A. multiple well overlay plot with U-II added at the arrow; B. average, from 6 wells, dose response curve for hU-II with an $EC_{50}$ of $7.875e^{-008}$; and C. average, from 6 wells, dose response curve for urantide with an $IC_{50}$ of $1.33e^{-009}$ (80 nM hU-II used).
Figure 7B:
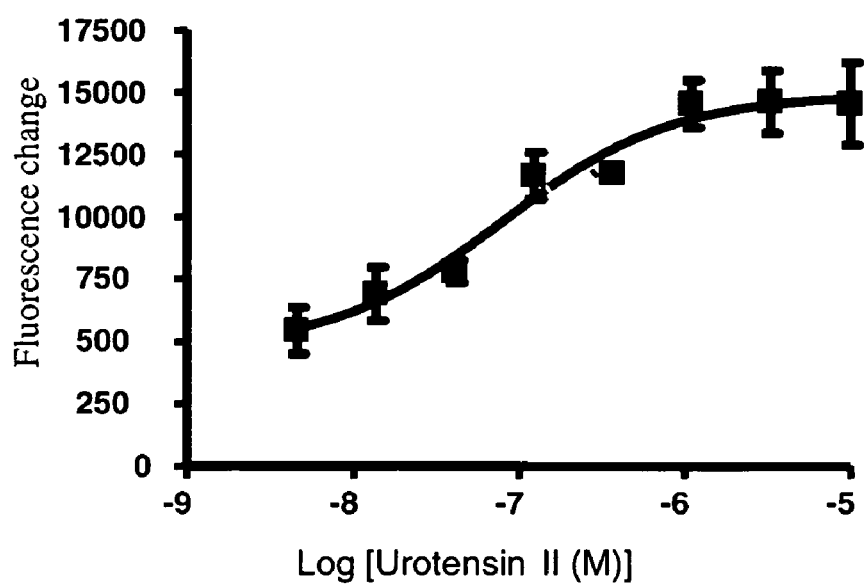
Figure 7:
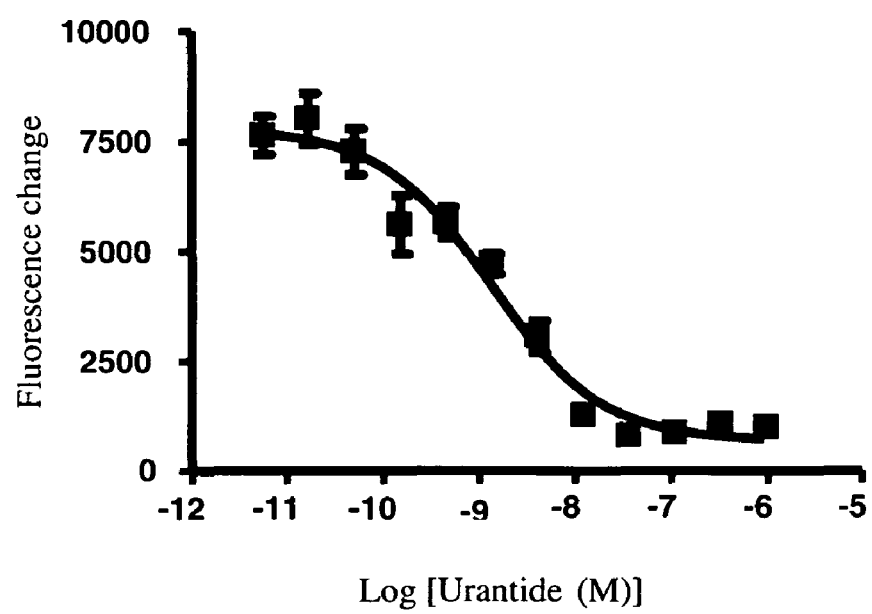

After optimizing the dye-loading time, cell density, and loading buffer composition, etc., consistent results (with Z' factor of greater than 0.5) were obtained from the 384-format high throughput assay (FIG. 7A). Using the HTS assay format, dose dependent responses had been observed for both UII, a compound that increases the biological activity of an UT receptor, and Urantide, a compound that decreases the biological activity of an UT receptor.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A human cell clone that is a sub-clone of SJRH30 (ATCC® Number: CRL-2061™), having at least about 50% more endogenous urotensin II binding sites cell$^{-1}$ than those of the parental SJRH30.

2. A cell culture comprising cells of a human cell clone that is a sub-clone of SJRH30 (ATCC® Number: CRL-2061™), having at least about 50% more endogenous urotensin II binding sites cell$^{-1}$ than those of the parental SJRH30.

3. A human cell clone having at least about 100% more endogenous urotensin II binding sites cell$^{-1}$ than those of the parental SJRH30.

4. The human cell clone of claim 3 that is the 4G5 cell clone (ATCC® Number: PTA-7747).

5. The human cell clone of claim 3 that is the 10A7 cell clone (ATCC® Number: PTA-7748).

6. The human cell clone of claim 3 that is the 6D9 cell clone (ATCC® Number: PTA-7749).

7. A cell culture comprising cells of a human cell clone that is a sub-clone of SJRH30 (ATCC® Number: CRL-2061™), having at least about 100% more endogenous urotensin II binding sites cell$^{-1}$ than those of the parental SJRH30.

8. The cell culture of claim 7 comprising cells of 4G5 cell clone (ATCC® Number: PTA-7747).

9. The cell culture of claim 7 comprising cells of 10A7 cell clone (ATCC® Number: PTA-7748).

10. The cell culture of claim 7 comprising cells of 6D9 cell clone (ATCC® Number: PTA-7749).

* * * * *

SEQUENCE LISTING

<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:
      Synthetic peptide

```
<400> SEQUENCE: 1

Cys Phe Trp Lys Tyr Cys
  1               5

<210> SEQ ID NO 2
<211> LENGTH: 11
<212> TYPE: PRT
<213> ORGANISM: Homo sapiens

<400> SEQUENCE: 2

Glu Thr Pro Asp Cys Phe Trp Lys Tyr Cys Val
  1               5                  10

<210> SEQ ID NO 3
<211> LENGTH: 13
<212> TYPE: PRT
<213> ORGANISM: Unknown Organism
<220> FEATURE:
<223> OTHER INFORMATION: Description of Unknown Organism: Frog
      sequence

<400> SEQUENCE: 3

Ala Gly Asn Leu Ser Glu Cys Phe Trp Lys Tyr Cys Val
  1               5                  10

<210> SEQ ID NO 4
<211> LENGTH: 12
<212> TYPE: PRT
<213> ORGANISM: Unknown Organism
<220> FEATURE:
<223> OTHER INFORMATION: Description of Unknown Organism: Trout
      sequence

<400> SEQUENCE: 4

Gly Gly Asn Ser Glu Cys Phe Trp Lys Tyr Cys Val
  1               5                  10

<210> SEQ ID NO 5
<211> LENGTH: 12
<212> TYPE: PRT
<213> ORGANISM: Cyprinus sp.

<400> SEQUENCE: 5

Gly Gly Gly Ala Glu Cys Phe Trp Lys Tyr Cys Val
  1               5                  10

<210> SEQ ID NO 6
<211> LENGTH: 12
<212> TYPE: PRT
<213> ORGANISM: Sus sp.

<400> SEQUENCE: 6

Gly Thr Pro Ser Glu Cys Phe Trp Lys Tyr Cys Val
  1               5                  10

<210> SEQ ID NO 7
<211> LENGTH: 12
<212> TYPE: PRT
<213> ORGANISM: Sus sp.

<400> SEQUENCE: 7

Gly Pro Pro Ser Glu Cys Phe Trp Lys Tyr Cys Val
  1               5                  10
```

```
<210> SEQ ID NO 8
<211> LENGTH: 13
<212> TYPE: PRT
<213> ORGANISM: Rattus sp.

<400> SEQUENCE: 8

His Gly Thr Ala Pro Glu Cys Phe Trp Lys Tyr Cys Ile
  1               5                  10

<210> SEQ ID NO 9
<211> LENGTH: 13
<212> TYPE: PRT
<213> ORGANISM: Mus sp.

<400> SEQUENCE: 9

His Gly Ala Ala Pro Glu Cys Phe Trp Lys Tyr Cys Ile
  1               5                  10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 10

Ala Cys Phe Trp Lys Tyr Cys Val
  1               5
```